United States Patent
Kossmann et al.

(10) Patent No.: US 6,307,124 B1
(45) Date of Patent: Oct. 23, 2001

(54) NUCLEIC ACID MOLECULES ENCODING SOLUBLE STARCH SYNTHASES FROM MAIZE

(75) Inventors: Jens Kossmann, Golm; Claus Frohberg, Berlin, both of (DE)

(73) Assignee: PlantTec Biotechnologie GmbH, Potsdam (DE)

( * ) Notice: Subject to any disclaimer, the term of this patent is extended or adjusted under 35 U.S.C. 154(b) by 0 days.

(21) Appl. No.: 09/192,909

(22) Filed: Nov. 16, 1998

Related U.S. Application Data

(63) Continuation of application No. PCT/EP97/02527, filed on May 16, 1997.

(30) Foreign Application Priority Data

May 17, 1996 (DE) .............................................. 196 19 918

(51) Int. Cl.$^7$ .............................. C12N 15/29; C12N 5/04; C12N 15/82; A01H 5/00; C12P 19/04
(52) U.S. Cl. ....................... 800/284; 800/278; 800/317.2; 800/320; 800/320.1; 800/320.2; 800/320.3; 536/23.6; 435/69.1; 435/320.1; 435/412; 435/419; 435/468
(58) Field of Search .......................... 536/23.6; 435/419, 435/412, 320.1, 69.1, 468; 800/278, 284, 320.1, 320, 320.2, 320.3, 317.2

(56) References Cited

U.S. PATENT DOCUMENTS

| 5,300,145 | 4/1994 | Fergason et al. ..................... 106/213 |
| 5,349,123 | * 9/1994 | Shewmaker et al. ................. 800/205 |
| 5,824,790 | * 10/1998 | Keeling et al. ...................... 536/23.6 |

FOREIGN PATENT DOCUMENTS

| 713978 | 6/1996 | (AU) . |
| 74268/96 | 7/1997 | (AU) . |
| 2061443 | 8/1993 | (CA) . |
| 43 30 960 A1 | 3/1995 | (DE) ................................ A01H/5/00 |
| 44 41 408 A1 | 5/1996 | (DE) .............................. C12N/15/82 |
| 6-70779 | 3/1994 | (JP) . |
| WO 92/11376 | 7/1992 | (WO) . |
| WO 94/09144 | 4/1994 | (WO) ............................. C12N/15/82 |
| WO 94/11520 | 5/1994 | (WO) . |
| WO 97/20936 | 6/1997 | (WO) ............................. C12N/15/52 |

OTHER PUBLICATIONS

Dry et al. Plant J. 2(2):193–202, 1992.*
Kossmann et al. Progress Biotechnol. 10:271–278, 1995.*
Gordon–Kamm et al. Plant cell 2:603–618, Jul. 1990.*

G.J.W. Abel, Untersuchungen zur Funktion von Stärke–Synthasen in der Kartoffel (*Solanum tuberosum* L.), PhD Thesis, Freie Universität Berlin (derfended Nov. 3, 1995).
A. Edwards et al., (1995) "Biochemical and Molecular Characterization of a Novel Starch Synthase from Potato Tubers," *Plant J.*, 8(2), pp. 283–294.
R.B. Klöosgen et al., "Molecular Analysis of the waxy Locus of *Zea mays*," *Molec. Gen. Genet.*, 203, pp. 237–244 (1986).
B. Müller–Röber et al., (1994) "Approaches to Infuence Starch Quanity and Starch Quality in Transgenic Plants," *Plant, Cell and Environment*, 17, pp. 601–613.
Nakatani et al., (1995) "Relationship between Starch Content and Activity of Starch Synthase and ADP–glucose Pyrophosphorylase in Tuberous Root of Sweet Potato" *Japanese J. Crop Sci.*, 61, pp. 463–468.
S.N.I.M. Salehuzzaman et al., "Isolation and Characterization of a cDNA Encloding Granule–Bound Starch Synthase In Cassava (*Manihot esculenta* Crantz) and its Antisense Expression in Potato", *Plant Molec. Biol.*, 23, pp. 947–962 (1993).
R.G.F. Visser et al., "Inhibition of the Expression of the Gene for Granule–bound Starch Synthase in Potato by Antisense Constructs," *Molec. Gen. Genet.*, 225, pp. 289–296 (1991).
T. Baba et al., "Identification, cDNA Cloning, and Gene Expression of Soluble Starch Synthase in Rice (*Oryza sativa* L.) Immature Seeds," *Plant Physiol.*, 103, pp. 565–573 (1993).
C. Harn et al., "Isolation of a Starch Synthase cDNA Clone from Maize Inbred Line W64A," *Plant Physiol.*, 108(2), p. 50, Abstract 187 (1995).
C. Mu et al., "Association of a 76 kDa Polypeptide with Soluble Starch Synthase 1 Activity in Maize (cvB73) Endosperm," *The Plant Journal*, 6(2), pp. 151–159 (1994).
Database WPI, AN 94–128678, Week 9416, *Derwent Publications Ltd.*, (Mar. 15, 1994).

* cited by examiner

*Primary Examiner*—David T. Fox
(74) *Attorney, Agent, or Firm*—Fish & Neave; James F. Haley, Jr.; Elinor K. Shin

(57) ABSTRACT

Nucleic acid molecules are described encoding enzymes involved in the starch synthesis in plants. These enzymes are a novel isotype of soluble starch synthesis from maize. Furthermore, the invention relates to vectors containing such nucleic acid molecules and to host cells, which have been transformed with the nucleic acid molecules, in particular to transformed plant cells or plants regenerable therefrom, which exhibit an increased or reduced activity of the described proteins.

27 Claims, 2 Drawing Sheets

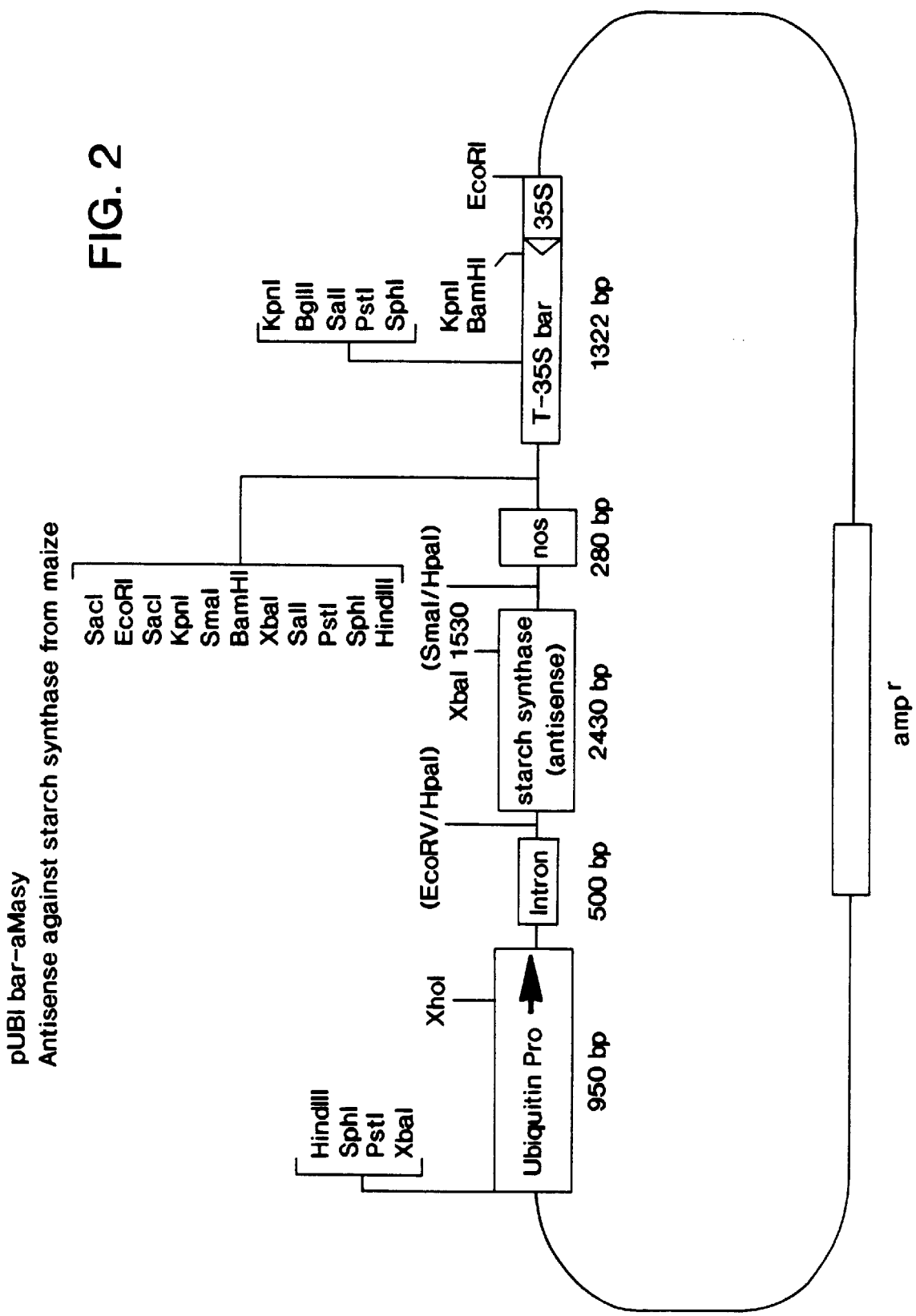

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
       (A) LENGTH: 2383 base pairs
       (B) TYPE: nucleotide
       (C) STRANDEDNESS: double
       (D) TOPOLOGY: linear (ii) MOLECULE TYPE: cDNA to mRNA (iii) HYPOTHETICAL: NO (iv) ANTI-SENSE: NO (vi) ORIGINAL SOURCE:
       (A) ORGANISM: Zea mays
       (F) TISSUE TYPE: endosperm (ix) FEATURE:
       (A) NAME/KEY: CDS
       (B) LOCATION: 2..1950
       (D) OTHER INFORMATION: /function= "starch synthesis"
           /product= "soluble starch synthase"

(xi) SEQUENCE DESCRIPTION: SEQ ID NO: 1:

```
G GCA CGA GGT CTG CTC TCC CTC TCC GCA ATG GCG ACG CCC TCG GCC      46
  Ala Arg Gly Leu Leu Ser Leu Ser Ala Met Ala Thr Pro Ser Ala
  1               5                  10                  15
```

```
GTG GGC GCC GCG TGC CTC CTC CTC GCG CGG GCC GCC TGG CCG GCC GCC        94
Val Gly Ala Ala Cys Leu Leu Leu Ala Arg Ala Ala Trp Pro Ala Ala
             20                  25                  30

GTC GGC GAC CGG GCG CGC CCG CGG CGG CTC CAG CGC GTG CTG CGC CGC       142
Val Gly Asp Arg Ala Arg Pro Arg Arg Leu Gln Arg Val Leu Arg Arg
             35                  40                  45

CGG TGC GTC GCG GAG CTG AGC AGG GAG GGC CCC GCG CCG CGC CCG ATG       190
Arg Cys Val Ala Glu Leu Ser Arg Glu Gly Pro Ala Pro Arg Pro Met
             50                  55                  60

CCA CCC GCG CTG CTG GCG CCC CCG CTC GTG CCC GGC TTC CTC GCG CCG       238
Pro Pro Ala Leu Leu Ala Pro Pro Leu Val Pro Gly Phe Leu Ala Pro
         65                  70                  75

CCG GCC GAG CCC ACG GGT GAG CCG GCA TTG ACG CCG CCG CCC GTG CCC       286
Pro Ala Glu Pro Thr Gly Glu Pro Ala Leu Thr Pro Pro Pro Val Pro
     80                  85                  90                  95

GAC GCC GGC CTG GGG GTC CTC GGT GTC GAA CCT GAA GGG ATT GCT GAA       334
Asp Ala Gly Leu Gly Val Leu Gly Val Glu Pro Glu Gly Ile Ala Glu
                100                 105                 110

GGT TCC ATC GAT AAC ACA GTA GTT GTG GCA AGT GAG CAA GAT TCT GAG       382
Gly Ser Ile Asp Asn Thr Val Val Val Ala Ser Glu Gln Asp Ser Glu
             115                 120                 125

ATT GTG GTT GGA AAG GAG CAA GCT CGA GCT AAA GTA ACA CAA AAC ATT       430
Ile Val Val Gly Lys Glu Gln Ala Arg Ala Lys Val Thr Gln Asn Ile
             130                 135                 140

GTC TTT GTA ACT GGC GAA GCT TCT CCT TAT GCA AAG TCT GGG GGT CTA       478
Val Phe Val Thr Gly Glu Ala Ser Pro Tyr Ala Lys Ser Gly Gly Leu
         145                 150                 155

GGA GAT GTT TGT GGT TCA TTG CCA GTT GCT CTT GCT GCT CGT GGT CAC       526
Gly Asp Val Cys Gly Ser Leu Pro Val Ala Leu Ala Ala Arg Gly His
160                 165                 170                 175

CGT GTG ATG GTT GTA ATG CCC AGA TAT TTA AAT GGT ACC TCC GAT AAG       574
Arg Val Met Val Val Met Pro Arg Tyr Leu Asn Gly Thr Ser Asp Lys
                180                 185                 190

AAT TAT GCA AAT GCA TTT TAC ACA GAA AAA CAC ATT CGG ATT CCA TGC       622
Asn Tyr Ala Asn Ala Phe Tyr Thr Glu Lys His Ile Arg Ile Pro Cys
             195                 200                 205

TTT GGC GGT GAA CAT GAA GTT ACC TTC TTC CAT GAG TAT AGA GAT TCA       670
Phe Gly Gly Glu His Glu Val Thr Phe Phe His Glu Tyr Arg Asp Ser
         210                 215                 220

GTT GAC TGG GTG TTT GTT GAT CAT CCC TCA TAT CAC AGA CCT GGA AAT       718
Val Asp Trp Val Phe Val Asp His Pro Ser Tyr His Arg Pro Gly Asn
         225                 230                 235

TTA TAT GGA GAT AAG TTT GGT GCT TTT GGT GAT AAT CAG TTC AGA TAC       766
Leu Tyr Gly Asp Lys Phe Gly Ala Phe Gly Asp Asn Gln Phe Arg Tyr
240                 245                 250                 255

ACA CTC CTT TGC TAT GCT GCA TGT GAG GCT CCT TTG GTC CTT GAA TTG       814
Thr Leu Leu Cys Tyr Ala Ala Cys Glu Ala Pro Leu Val Leu Glu Leu
             260                 265                 270

GGA GGA TAT ATT TAT GGA CAG AAT TGC ATG TTT GTT GTC AAT GAT TGG       862
Gly Gly Tyr Ile Tyr Gly Gln Asn Cys Met Phe Val Val Asn Asp Trp
             275                 280                 285

CAT GCC AGT CTA GTG CCA GTC CTT CTT GCT GCA AAA TAT AGA CCA TAT       910
His Ala Ser Leu Val Pro Val Leu Leu Ala Ala Lys Tyr Arg Pro Tyr
         290                 295                 300

GGT GTT TAT AAA GAC TCC CGC AGC ATT CTT GTA ATA CAT AAT TTA GCA       958
Gly Val Tyr Lys Asp Ser Arg Ser Ile Leu Val Ile His Asn Leu Ala
         305                 310                 315

CAT CAG GGT GTA GAG CCT GCA AGC ACA TAT CCT GAC CTT GGG TTG CCA      1006
His Gln Gly Val Glu Pro Ala Ser Thr Tyr Pro Asp Leu Gly Leu Pro
```

```
                320                 325                 330                 335
CCT GAA TGG TAT GGA GCT CTG GAG TGG GTA TTC CCT GAA TGG GCG AGG              1054
Pro Glu Trp Tyr Gly Ala Leu Glu Trp Val Phe Pro Glu Trp Ala Arg
                340                 345                 350

AGG CAT GCC CTT GAC AAG GGT GAG GCA GTT AAT TTT TTG AAA GGT GCA              1102
Arg His Ala Leu Asp Lys Gly Glu Ala Val Asn Phe Leu Lys Gly Ala
                355                 360                 365

GTT GTG ACA GCA GAT CGA ATC GTG ACT GTC AGT AAG GGT TAT TCA TGG              1150
Val Val Thr Ala Asp Arg Ile Val Thr Val Ser Lys Gly Tyr Ser Trp
                370                 375                 380

GAG GTC ACA ACT GCT GAA GGT GGA CAG GGC CTC AAT GAG CTC TTA AGC              1198
Glu Val Thr Thr Ala Glu Gly Gly Gln Gly Leu Asn Glu Leu Leu Ser
                385                 390                 395

TCC AGA AAG AGT GTA TTA AAC GGA ATT GTA AAT GGA ATT GAC ATT AAT              1246
Ser Arg Lys Ser Val Leu Asn Gly Ile Val Asn Gly Ile Asp Ile Asn
400                 405                 410                 415

GAT TGG AAC CCT GCC ACA GAC AAA TGT ATC CCC TGT CAT TAT TCT GTT              1294
Asp Trp Asn Pro Ala Thr Asp Lys Cys Ile Pro Cys His Tyr Ser Val
                420                 425                 430

GAT GAC CTC TCT GGA AAG GCC AAA TGT AAA GGT GCA TTG CAG AAG GAG              1342
Asp Asp Leu Ser Gly Lys Ala Lys Cys Lys Gly Ala Leu Gln Lys Glu
                435                 440                 445

CTG GGT TTA CCT ATA AGG CCT GAT GTT CCT CTG ATT GGC TTT ATT GGA              1390
Leu Gly Leu Pro Ile Arg Pro Asp Val Pro Leu Ile Gly Phe Ile Gly
                450                 455                 460

AGA TTG GAT TAT CAG AAA GGC ATT GAT CTC ATT CAA CTT ATC ATA CCA              1438
Arg Leu Asp Tyr Gln Lys Gly Ile Asp Leu Ile Gln Leu Ile Ile Pro
                465                 470                 475

GAT CTC ATG CGG GAA GAT GTT CAA TTT GTC ATG CTT GGA TCT GGT GAC              1486
Asp Leu Met Arg Glu Asp Val Gln Phe Val Met Leu Gly Ser Gly Asp
480                 485                 490                 495

CCA GAG CTT GAA GAT TGG ATG AGA TCT ACA GAG TCG ATC TTC AAG GAT              1534
Pro Glu Leu Glu Asp Trp Met Arg Ser Thr Glu Ser Ile Phe Lys Asp
                500                 505                 510

AAA TTT CGT GGA TGG GTT GGA TTT AGT GTT CCA GTT TCC CAC CGA ATA              1582
Lys Phe Arg Gly Trp Val Gly Phe Ser Val Pro Val Ser His Arg Ile
                515                 520                 525

ACT GCC GGC TGC GAT ATA TTG TTA ATG CCA TCC AGA TTC GAA CCT TGT              1630
Thr Ala Gly Cys Asp Ile Leu Leu Met Pro Ser Arg Phe Glu Pro Cys
                530                 535                 540

GGT CTC AAT CAG CTA TAT GCT ATG CAG TAT GGC ACA GTT CCT GTT GTC              1678
Gly Leu Asn Gln Leu Tyr Ala Met Gln Tyr Gly Thr Val Pro Val Val
                545                 550                 555

CAT GCA ACT GGG GGC CTT AGA GAT ACC GTG GAG AAC TTC AAC CCT TTC              1726
His Ala Thr Gly Gly Leu Arg Asp Thr Val Glu Asn Phe Asn Pro Phe
560                 565                 570                 575

GGT GAG AAT GGA GAG CAG GGT ACA GGG TGG GCA TTC GCA CCC CTA ACC              1774
Gly Glu Asn Gly Glu Gln Gly Thr Gly Trp Ala Phe Ala Pro Leu Thr
                580                 585                 590

ACA GAA AAC ATG TTG TGG ACA TTG CGA ACT GCA ATA TCT ACA TAC AGG              1822
Thr Glu Asn Met Leu Trp Thr Leu Arg Thr Ala Ile Ser Thr Tyr Arg
                595                 600                 605

GAA CAC AAG TCC TCC TGG GAA GGG CTA ATG AAG CGA GGC ATG TCA AAA              1870
Glu His Lys Ser Ser Trp Glu Gly Leu Met Lys Arg Gly Met Ser Lys
                610                 615                 620

GAC TTC ACG TGG GAC CAT GCC GCT GAA CAA TAC GAA CAA ATC TTC CAG              1918
Asp Phe Thr Trp Asp His Ala Ala Glu Gln Tyr Glu Gln Ile Phe Gln
                625                 630                 635

TGG GCC TTC ATC GAT CGA CCC TAT GTC ATG TA AAAAAGGACC AAAGTGGTGG             1970
Trp Ala Phe Ile Asp Arg Pro Tyr Val Met
```

-continued

```
Trp Ala Phe Ile Asp Arg Pro Tyr Val Met
640                 645

TTCCTTGAAG ATCATCAGTT CATCATCCTA TAGTAAGCTG AATGATGAAA GAAAACCCCT      2030

GTACATTACA TGGAAGGCAG ACCGGCTATT GGCTCCATTG CTCCAATGTC TGCTTTGGCT      2090

GCCTTGCCTC GATGGACCGG ATGCAGTGAG GAATCCAGCC GAACGACAGT TTTGAAGGAT      2150

AGGAAGGGGA GCTGGAAGCA GTCACGCAGG CAGCCTCGCC GTGATTCATA TGGAACAAGC      2210

TGGAGTCAGT TTCTGCTGTG CCACTCACTG TTTACCTTAA GATTATTACC TGTGTTGTTG      2270

TCCTTTGCTC GTTAGGGCTG ATAACATAAT GACTCATTAG AAAATCATGC CTCGTTTTTA      2330

TTAACTGAAG TGGACACTTC GCATTCTTGC CCGTTTAAAA AAAAAAAAA AAA              2383

(2) INFORMATION FOR SEQ ID NO: 2:

(i) SEQUENCE CHARACTERISTICS:
        (A) LENGTH: 649 amino acids
        (B) TYPE: amino acid
        (D) TOPOLOGY: linear (ii) MOLECULE TYPE: protein (xi) SEQUENCE DESCRIPTION: SEQ ID NO: 2:

Ala Arg Gly Leu Leu Ser Leu Ser Ala Met Ala Thr Pro Ser Ala Val
1               5                   10                  15

Gly Ala Ala Cys Leu Leu Leu Ala Arg Ala Ala Trp Pro Ala Ala Val
                20                  25                  30

Gly Asp Arg Ala Arg Pro Arg Arg Leu Gln Arg Val Leu Arg Arg Arg
            35                  40                  45

Cys Val Ala Glu Leu Ser Arg Glu Gly Pro Ala Pro Arg Pro Met Pro
    50                  55                  60

Pro Ala Leu Leu Ala Pro Pro Leu Val Pro Gly Phe Leu Ala Pro Pro
65                  70                  75                  80

Ala Glu Pro Thr Gly Glu Pro Ala Leu Thr Pro Pro Val Pro Asp
                85                  90                  95

Ala Gly Leu Gly Val Leu Gly Val Glu Pro Glu Gly Ile Ala Glu Gly
                100                 105                 110

Ser Ile Asp Asn Thr Val Val Ala Ser Glu Gln Asp Ser Glu Ile
        115                 120                 125

Val Val Gly Lys Glu Gln Ala Arg Ala Lys Val Thr Gln Asn Ile Val
    130                 135                 140

Phe Val Thr Gly Glu Ala Ser Pro Tyr Ala Lys Ser Gly Gly Leu Gly
145                 150                 155                 160

Asp Val Cys Gly Ser Leu Pro Val Ala Leu Ala Ala Arg Gly His Arg
                165                 170                 175

Val Met Val Val Met Pro Arg Tyr Leu Asn Gly Thr Ser Asp Lys Asn
            180                 185                 190

Tyr Ala Asn Ala Phe Tyr Thr Glu Lys His Ile Arg Ile Pro Cys Phe
        195                 200                 205

Gly Gly Glu His Glu Val Thr Phe Phe His Glu Tyr Arg Asp Ser Val
    210                 215                 220

Asp Trp Val Phe Val Asp His Pro Ser Tyr His Arg Pro Gly Asn Leu
225                 230                 235                 240

Tyr Gly Asp Lys Phe Gly Ala Phe Gly Asp Asn Gln Phe Arg Tyr Thr
                245                 250                 255

Leu Leu Cys Tyr Ala Ala Cys Glu Ala Pro Leu Val Leu Glu Leu Gly
            260                 265                 270
```

```
Gly Tyr Ile Tyr Gly Gln Asn Cys Met Phe Val Val Asn Asp Trp His
            275                 280                 285

Ala Ser Leu Val Pro Val Leu Leu Ala Ala Lys Tyr Arg Pro Tyr Gly
        290                 295                 300

Val Tyr Lys Asp Ser Arg Ser Ile Leu Val Ile His Asn Leu Ala His
305                 310                 315                 320

Gln Gly Val Glu Pro Ala Ser Thr Tyr Pro Asp Leu Gly Leu Pro Pro
                325                 330                 335

Glu Trp Tyr Gly Ala Leu Glu Trp Val Phe Pro Glu Trp Ala Arg Arg
            340                 345                 350

His Ala Leu Asp Lys Gly Glu Ala Val Asn Phe Leu Lys Gly Ala Val
        355                 360                 365

Val Thr Ala Asp Arg Ile Val Thr Val Ser Lys Gly Tyr Ser Trp Glu
370                 375                 380

Val Thr Thr Ala Glu Gly Gly Gln Gly Leu Asn Glu Leu Leu Ser Ser
385                 390                 395                 400

Arg Lys Ser Val Leu Asn Gly Ile Val Asn Gly Ile Asp Ile Asn Asp
            405                 410                 415

Trp Asn Pro Ala Thr Asp Lys Cys Ile Pro Cys His Tyr Ser Val Asp
        420                 425                 430

Asp Leu Ser Gly Lys Ala Lys Cys Lys Gly Ala Leu Gln Lys Glu Leu
        435                 440                 445

Gly Leu Pro Ile Arg Pro Asp Val Pro Leu Ile Gly Phe Ile Gly Arg
    450                 455                 460

Leu Asp Tyr Gln Lys Gly Ile Asp Leu Ile Gln Leu Ile Ile Pro Asp
465                 470                 475                 480

Leu Met Arg Glu Asp Val Gln Phe Val Met Leu Gly Ser Gly Asp Pro
            485                 490                 495

Glu Leu Glu Asp Trp Met Arg Ser Thr Glu Ser Ile Phe Lys Asp Lys
                500                 505                 510

Phe Arg Gly Trp Val Gly Phe Ser Val Pro Val Ser His Arg Ile Thr
        515                 520                 525

Ala Gly Cys Asp Ile Leu Leu Met Pro Ser Arg Phe Glu Pro Cys Gly
    530                 535                 540

Leu Asn Gln Leu Tyr Ala Met Gln Tyr Gly Thr Val Pro Val Val His
545                 550                 555                 560

Ala Thr Gly Gly Leu Arg Asp Thr Val Glu Asn Phe Asn Pro Phe Gly
            565                 570                 575

Glu Asn Gly Glu Gln Gly Thr Gly Trp Ala Phe Ala Pro Leu Thr Thr
                580                 585                 590

Glu Asn Met Leu Trp Thr Leu Arg Thr Ala Ile Ser Thr Tyr Arg Glu
        595                 600                 605

His Lys Ser Ser Trp Glu Gly Leu Met Lys Arg Gly Met Ser Lys Asp
    610                 615                 620

Phe Thr Trp Asp His Ala Ala Glu Gln Tyr Glu Gln Ile Phe Gln Trp
625                 630                 635                 640

Ala Phe Ile Asp Arg Pro Tyr Val Met
            645
```

(2) INFORMATION FOR SEQ ID NO: 3:

(i) SEQUENCE CHARACTERISTICS:
        (A) LENGTH: 12 amino acids
        (B) TYPE: amino acid

```
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal fragment (xi) SEQUENCE DESCRIPTION: SEQ ID NO: 3:

Gly Thr Gly Gly Leu Arg Asp Thr Val Glu Asn Cys
1               5                   10
```

NUCLEIC ACID MOLECULES ENCODING SOLUBLE STARCH SYNTHASES FROM MAIZE

This application is a continuation of international application PCT/EP97/02527, filed on May 16, 1997, which designated the United States.

FIELD OF THE INVENTION

The present invention relates to nucleic acid molecules encoding a type of soluble starch synthase from maize.

Furthermore, the present invention relates to vectors and bacteria, as well as to plant cells transformed with the described nucleic acid molecules and to plants regenerable from these cells.

Furthermore, methods for producing transgenic plants are described which, due to the introduction of DNA molecules encoding a soluble starch synthase from maize, synthesize a starch modified in its properties.

With respect to the increasing significance which has recently been ascribed to vegetal substances as regenerative sources of raw materials, one of the objects of biotechnological research is to try to adapt vegetal raw materials to the demands of the processing industry. In order to enable the use of regenerative raw materials in as many areas as possible, it is furthermore important to obtain a large variety of substances.

Apart from oils, fats and proteins, polysaccharides constitute the essential regenerative raw materials derived from plants. Apart from cellulose, starch maintains an important position among the polysaccharides, being one of the most significant storage substances in higher plants. Among those, maize is one of the most interesting plants as it is the most important cultivated plant for the production of starch.

The polysaccharide starch is a polymer made up of chemically homogeneous basic components, namely the glucose molecules. However, it constitutes a highly complex mixture from various types of molecules which differ from each other in their degree of polymerization and in the degree of branching of the glucose chains. Therefore, starch is not a homogeneous raw material. One differentiates particularly between amylose-starch, a basically non-branched polymer made up of α-1,4-glycosidically branched glucose molecules, and amylopectin-starch which in turn is a complex mixture of various branched glucose chains. The branching results from additional α-1,6-glycosidic interlinkings. In plants used typically for the production of starch, such as maize or potato, the synthesized starch consists of approximately 25% amylose-starch and of about 75% amylopectin-starch.

In order to enable as wide a use of starch as possible, it seems to be desirable that plants be provided which are capable of synthesizing modified starch which is particularly suitable for various uses. One possibility to provide such plants—apart from breeding methods—is the specific genetic modification of the starch metabolism of starch-producing plants by means of recombinant DNA techniques. However, a prerequisite for this is to identify and to characterize the enzymes involved in the starch synthesis and/or the starch modification as well as to isolate the respective DNA molecules encoding these enzymes.

The biochemical pathways which lead to the production of starch are basically known. The starch synthesis in plant cells takes place in the plastids. In photosynthetically active tissues these are the chloroplasts, in photosynthetically inactive, starch-storing tissues the amyloplasts.

The most important enzymes involved in starch synthesis are starch synthesis as well as branching enzymes. In the case of starch synthesis various isotypes are described which all catalyze a polymerization reaction by transferring a glycosyl residue of ADP-glucose to α-1,4-glucans. Branching enzymes catalyze the introduction of α-1,6 branchings into linear α-1,4-glucans.

Starch synthesis may be divided up in two groups: the granule-bound starch synthesis (GBSS) and the soluble starch synthesis (SSS). This distinction is not always evident since some starch synthesis are granule-bound as well as soluble (Denyer et al., Plant J. 4 (1993), 191–198; Mu et al., Plant J. 6 (1994), 151–159). Within these classifications, various isotypes are described for various species of plants. These isotypes differ from each other in their dependency on primer molecules (so-called "primer dependent" (type II) and "primer independent" (type I) starch synthesis).

So far only in the case of the isotype GBSS I its exact function during starch synthesis has been successfully determined. Plants in which this enzyme activity has been strongly or completely reduced, synthesize starch free of amylose (a so-called "waxy" starch) (Shure et al., Cell 35 (1983), 225–233; Visser et al., Mol. Gen. Genet. 225 (1991), 289–296; WO 92/11376); therefore this enzyme has been assigned a decisive role in synthesizing amylose-starch. This phenomenon is also observed in the cells of the green alga *Chlamydomonas reinhardtii* (Delrue et al., J. Bacteriol. 174 (1992), 3612–3620). In the case of Chlamydomonas it was furthermore demonstrated that GBSS I is not only involved in the synthesis of amylose but also has a certain influence on amylopectin synthesis. In mutants which do not show any GBSS I activity a particular fraction of the normally synthesized amylopectin, exhibiting long chain glucans, is missing.

The functions of the other isotypes of the granule-bound starch synthesis, particularly GBSS II, and of the soluble starch synthesis are so far not clear. It is assumed that soluble starch synthesis, together with branching enzymes, are involved in the synthesis of amylopectin (see e.g. Ponstein et al., Plant Physiol. 92 (1990), 234–241) and that they play an important role in the regulation of starch synthesis rate.

In the case of maize, two isotypes of granule-bound starch synthase as well as two or three isotypes of the soluble starch synthases have been identified (Hawker et al., Arch. Biochem. Biophys. 160 (1974), 530–551; Pollock and Preiss, Arch. Biochem. Biophys. 204 (1980), 578–588; MacDonald and Preiss, Plant Physiol. 78 (1985), 849–852; Mu et al., Plant J. 6 (1994), 151–159).

A cDNA encoding GBSS I from maize as well as a genomic DNA have already been described (Shure et al., Cell 35 (1983), 225–233; Kloesgen et al., Mol. Gen. Genet. 203 (1986), 237–244). Furthermore, a so-called "Expressed Sequence Tag" (EST) has been described (Shen et al., 1994, GenBank No.: T14684); the amino acid sequence derived therefrom exhibits a strong similarity to the amino acid sequence derived from the GBSS II from pea (Dry et al., Plant J. 2 (1992), 193–202) and potato (Edwards et al., Plant J. 8 (1995), 283–294). Nucleic acid sequences encoding further starch synthase isotypes from maize have not been described so far. cDNA sequences coding for starch synthases other than GBSS I have so far only been described for pea (Dry et al., Plant J. 2 (1992), 193–202), rice (Baba et al., Plant Physiol. 103 (1993), 565–573) and potato (Edwards et al., Plant J. 8 (1995), 283–294).

Soluble starch synthases have been identified in several other plant species apart from maize. Soluble starch synthases have for example been isolated in homogeneous form from pea (Denyer and Smith, Planta 186 (1992), 609–617) and potatoes (Edwards et al., Plant J. 8 (1995), 283–294). In these cases it was found that the isotype of the soluble starch synthase identified as SSS II is identical with the granule-bound starch synthase GBSS II (Denyer et al., Plant J. 4 (1993), 191–198; Edwards et al., Plant J. 8 (1995), 283–294). In the case of some other plant species the existence of several SSS-isotypes was described by means of chromatographic methods, as for example in the case of barley (Tyynelä and Schulman, Physiologia Plantarum 89 (1993), 835–841; Kreis, Planta 148 (1980), 412–416) and wheat (Rijven, Plant Physiol. 81 (1986), 448453). However, DNA sequences encoding these proteins have so far not been described.

In order to provide further possibilities for modifying any desired starch-storing plant in such a way that they will synthesize a modified starch, respective DNA sequences encoding further isotypes of starch synthases have to be identified.

Therefore, the technical problem underlying the present invention is to provide nucleic acid molecules encoding enzymes involved in starch biosynthesis and by means of which genetically modified plants may be produced that show an increased or reduced activity of those enzymes, thereby prompting a modification in the chemical and/or physical properties of the starch synthesized in these plants.

This problem is solved by the provision of the embodiments described in the claims.

SUMMARY OF THE INVENTION

Therefore, the present invention relates to nucleic acid molecules encoding proteins with the biological activity of a type I soluble starch synthase from maize, wherein such molecules preferably encode proteins which comprise the amino acid sequence depicted under Seq ID No. 2. The invention particularly relates to nucleic acid molecules which comprise all or part of the nucleotide sequence mentioned under Seq ID No. 1, preferably molecules, which comprise the coding region indicated in Seq ID No. 1 or, as the case may be, corresponding ribonucleotide sequences.

The present invention further relates to nucleic acid molecules which encode a soluble starch synthase from maize and one strand of which hybridizes to one of the above-mentioned molecules or to a complementary strand of said molecules.

Nucleic acid molecules that encode type I soluble starch synthase from maize and the sequence of which differs from the nucleotide sequences of the above-mentioned molecules due to the degeneracy of the genetic code are also the subject-matter of the invention.

The invention also relates to nucleic acid molecules showing a sequence which is complementary to the whole or to a part of the sequence of the above-mentioned molecules.

The nucleic acid molecules of the invention may be DNA as well as RNA molecules. Corresponding DNA molecules are for instance genomic or cDNA molecules. In this invention the term "hybridization" signifies hybridization under conventional hybridizing conditions, preferably under stringent conditions as described for example in Sambrook et al., Molecular Cloning, A Laboratory Manual, 2nd Edition (1989) Cold Spring Harbor Laboratory Press, Cold Spring Harbor, N.Y.).

Nucleic acid molecules which hybridize with the nucleic acid molecules according to the invention can in principle be derived from any desired maize plant which comprises such molecules.

Nucleic acid molecules hybridizing to the nucleic acid molecules of the invention may be isolated e.g. from genomic or from cDNA libraries from maize plants or maize plant tissue. Alternatively, they can be produced by recombinant DNA techniques or by chemical synthesis.

The identification and isolation of such nucleic acid molecules may take place by using the molecules of the invention or parts of these molecules or, as the case may be, the reverse complement strands of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.).

As a probe for hybridization e.g. nucleic acid molecules may be used which exactly or basically contain the nucleotide sequence indicated under Seq ID No. 1 or parts thereof. The fragments used as hybridization probe may also be synthetic fragments which were produced by means of the conventional synthesizing methods and the sequence of which is basically identical with that of a nucleic acid molecule according to the invention. After identifying and isolating genes hybridizing to the nucleic acid sequences according to the invention, the sequence has to be determined and the properties of the proteins encoded by this sequence have to be analyzed.

The molecules hybridizing to the nucleic acid molecules of the invention also comprise fragments, derivatives and allelic variants of the above-described nucleic acid molecules which encode a soluble starch synthase from maize as described in the invention. Thereby, fragments are defined as parts of the nucleic acid molecules, which are long enough in order to encode one of the described proteins. In this context, the term derivatives means that the sequences of these molecules differ from the sequences of the above-mentioned nucleic acid molecules at one or more positions and that they exhibit a high degree of homology to these sequences. In this context, homology means a sequence identity of at least 40%, in particular an identity of at least 60%, preferably of more than 80% and still more preferably a sequence identity of more than 90%. The deviations occurring when comparing with the above-described nucleic acid molecules might have been caused by deletion, substitution, insertion or recombination.

Moreover, homology means that functional and/or structural equivalence exists between the respective nucleic acid molecules or the proteins they encode. The nucleic acid molecules, which are homologous to the above-described molecules and represent derivatives of these molecules, are generally variations of these molecules that constitute modifications which exert the same biological function. These variations may be naturally occurring variations, for example sequences derived from other maize varieties, or mutations, wherein these mutations may have occurred naturally or they may have been introduced by means of a specific mutagenesis. Moreover the variations may be synthetically produced sequences. The allelic variants may be naturally occurring as well as synthetically produced variants or variants produced by recombinant DNA techniques.

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability; pH-optimum, temperatureoptimum etc. Significant characteristics of a starch synthase are: i) its localization within the stroma of the plastids of plant cells; ii) its capability of synthesizing linear α-1,4-linked polyglucans using ADP-glucose as substrate. This activity can be determined as shown in Denyer and Smith (Planta 186 (1992), 606–617) or as described in the examples.

The proteins encoded by the nucleic acid molecules of the invention are a so far unidentified and uncharacterized type of soluble starch synthase from maize which may be classified as a type I ("primer independent"). Such starch synthases or nucleic acid molecules encoding such proteins have so far not been described from maize. The encoded protein exhibits a certain homology to a soluble starch synthase from rice (Baba et al., Plant Physiol. 103 (1993), 565–573).

Oligonucleotides hybridizing specifically to one of the nucleic acid molecules of the invention are also subject-matter of the invention. Such oligonucleotides preferably have a length of at least 10, particularly of at least 15 and still more preferably have a length of at least 50 nucleotides. They are characterized in that they hybridize specifically to the nucleic acid molecules of the invention, i.e. they do not or only to a small extent hybridize to nucleic acid sequences encoding other proteins, particularly other starch synthases. The oligonucleotides of the invention may be used for example as primers for a PCR. They may also be components of antisense-constructs or DNA molecules encoding suitable ribozymes.

Furthermore, the invention relates to vectors, especially plasmids, cosmids, viruses, bacteriophages and other vectors common in genetic engineering, which contain the above-mentioned nucleic acid molecules of the invention.

In a preferred embodiment the nucleic acid molecules contained in the vectors are linked to regulatory elements that ensure the transcription and synthesis of a translatable RNA in prokaryotic or eukaryotic cells.

The expression of the nucleic acid molecules of the invention in prokaryotic cells, e.g. in *Escherichia coli*, is interesting insofar as this enables a more precise characterization of the enzymatic activities of the enzymes encoded by these molecules. In particular, it is possible to characterize the product being synthesized by the respective enzymes in the absence of other enzymes which are involved in the starch synthesis in the plant cell. This makes it possible to draw conclusions about the function, which the respective protein exerts during the starch synthesis within the plant cell.

Moreover, it is possible to introduce various mutations into the nucleic acid molecules of the invention by means of conventional molecular-biological techniques (see e.g. Sambrook et al., 1989, Molecular Cloning, A Laboratory Manual, 2nd Edition, Cold Spring Harbor Laboratory Press, Cold Spring Harbor, N.Y.), which leads to the synthesis of proteins with possibly modified biological properties. By means of this it is on the one hand possible to produce deletion mutants, in which nucleic acid molecules are produced by continuing deletions at the 5'- or the 3'-end of the encoding DNA-sequence. These nucleic acid molecules may lead to the synthesis of correspondingly shortened proteins. Such deletions at the 5'-end of the nucleotide sequence make it possible, for example, to identify amino acid sequences which are responsible for the translocation of the enzyme in the plastids (transit peptides). This allows for the specific production of enzymes which due to the removal of the respective sequences are no longer located in the plastids but within the cytosol, or which due to the addition of other signal sequences are located in other compartments.

On the other hand point mutations may also be introduced at positions where a modification of the amino acid sequence influences, for example, the enzyme activity or the regulation of the enzyme. In this way e.g. mutants with a modified $K_m$-value may be produced, or mutants which are no longer subject to the regulation mechanisms by allosteric regulation or covalent modification usually occurring in cells.

Furthermore, mutants may be produced exhibiting a modified substrate or product specificity, such as mutants that utilize ADP-glucose-6-phosphate as a substrate instead of ADP-glucose. Moreover, mutants with a modified activity-temperature-profile may be produced.

For the genetic manipulation in prokaryotic cells the nucleic acid molecules of the invention or parts of these molecules may be integrated into plasmids which allow for a mutagenesis or a sequence modification by recombination of DNA sequences. By means of standard methods (cf. Sambrook et al., 1989, Molecular Cloning: A laboratory manual, 2nd edition, Cold Spring Harbor Laboratory Press, NY, USA) base exchanges may be carried out or natural or synthetic sequences may be added. In order to connect the DNA fragments with each other, adapters or linkers may be attached to the fragments. Moreover, use can be made of manipulations which offer suitable restriction sites or which remove superfluous DNA or restriction sites. Wherever use is made of insertions, deletions or substitutions, in vitro mutagenesis, "primer repair" restriction or ligation may be used. For analyzing use is usually made of a sequence analysis, a restriction analysis or further biochemico-molecularbiological methods.

In a further embodiment the invention relates to host cells, in particular to prokaryotic or eukaryotic cells, which have been transformed by an above-mentioned nucleic acid molecule of the invention or by a vector of the invention, as well as cells derived from cells transformed in such a way and containing a nucleic acid molecule of the invention or a vector of the invention. This is preferably a bacterial cell or a plant cell.

Furthermore, the proteins encoded by the nucleic acid molecules of the invention are the subject-matter of the invention as well as methods for their production in which a host cell of the invention is cultivated under conditions that allow for the synthesis of the protein and in which the protein is subsequently isolated from the cultivated cells and/or the culture medium.

Thus, the present invention also relates to transgenic plant cells which have been transformed, i.e. genetically modified with a nucleic acid molecule of the invention, as well as to transgenic plant cells which are derived from cells transformed in such a way and which contain the nucleic acid molecules of the invention.

By the provision of the nucleic acid molecules of the invention it is now possible—by means of recombinant DNA techniques—to interfere with the starch metabolism of plants in a way so far impossible. Thereby, the starch metabolism may be modified in such a way that a modified starch is synthesized which e.g. is modified, compared to the starch synthesized in wildtype plants, with respect to its physico-chemical properties, especially the amylose/amylopectin ratio, the degree of branching, the average chain length, the phosphate content, the pastification behavior, the size of the starch granule and/or the shape of the starch granule. There is the possibility of increasing the yield of genetically modified plants by increasing the activity of the proteins of the invention, e.g. by overexpressing the respective nucleic acid molecules or by making mutants available which are no longer subject to cell-specific regulation schemes and/or different temperature-dependencies with respect to their activity. The economic significance of the chance to interfere with the starch synthesis of maize alone is obvious: maize is the world's most important plant with regard to the production of starch. Approximately 80% of the starch globally produced each year is derived from maize.

Therefore it is possible to express the nucleic acid molecules of the invention in plant cells in order to increase the activity of the respective soluble starch synthase. Furthermore, the nucleic acid molecules of the invention may be modified by means of methods known to the skilled person, in order to produce starch synthases according to the invention which are no longer subject to the cell-specific regulation mechanisms or show modified temperature-dependencies or substrate or product specificities.

The cells of the invention contain a nucleic acid molecule of the invention, wherein this is preferably linked to regulatory DNA elements, which ensure the transcription in plant cells, especially with a promoter. Such cells differ from naturally occurring plant cells in that they contain a nucleic acid molecule of the invention which does not naturally occur in such cells or in that such a molecule is integrated at some position in the genome of the cell at which it does not naturally occur, i.e. in a different genomic environment.

In expressing the nucleic acid molecules of the invention in plants the synthesized proteins may in principle be located in any desired compartment within the plant cell.

In order to locate it within a specific compartment, the sequence ensuring the localization in the plastids must be deleted and the remaining coding region optionally has to be linked to DNA sequences which ensure localization in the respective compartment. Such sequences are known (see e.g. Braun et al., EMBO J. 11 (1992), 3219–3227; Wolter et al., Proc. Natl. Acad. Sci. USA 85 (1988), 846–850; Sonnewald et a., Plant J. 1 (1991), 95–106).

A further subject-matter of the invention are plants which contain the cells of the invention. These may be obtained e.g. by regenerating the transgenic plant cells of the invention by means of methods known to the skilled person. The transgenic plants may in principle be plants of any desired species, i.e. they may be monocotyledonous as well as dicotyledonous plants. These are preferably useful plants, in particular starch-synthesizing or starch-storing plants such as cereals (rye, barley, oats, wheat etc.), rice, maize, pea, cassava or potato.

The invention also relates to propagation material of the plants of the invention which contains the cells of the invention, such as fruits, seeds, tubers, root-stocks, seedlings, cuttings, calli, cell cultures etc.

The starch obtainable from the transgenic plant cells, plants and propagation material of the invention is a further subject-matter of the present invention.

Due to the expression or, as the case may be, additional expression of a nucleic acid molecule of the invention, the transgenic plant cells and plants of the invention synthesize a starch which compared to starch synthesized in wildtype plants is modified for example in its physico-chemical properties, in particular in the amylose/amylopectin ratio, the degree of branching, the average chain-length, the phosphate-content, the pastification behavior, the size of the starch granule and/or the shape of the starch granule. Compared with wildtype-starch, such starch may be modified in particular with respect to its viscosity and/or the gel formation properties of the glues of this starch.

Transgenic maize plant cells, in which the activity of a protein according to the invention is reduced when compared to non-transformed cells, are a further subject-matter of the invention.

It is possible by means of the nucleic acid molecules of the invention to produce maize plant cells and maize plants, in which the activity of the protein of the invention is reduced. This leads to the synthesis of a starch which, when compared to starch from wildtype plant cells, is modified in its chemical and/or physical properties.

The production of maize plant cells with a reduced activity of a protein of the invention may for example be achieved by the expression of a corresponding antisense-RNA, of a sense-RNA for achieving a cosuppression effect or the expression of a correspondingly constructed ribozyme, which specifically cleaves transcripts encoding one of the proteins of the invention, using the nucleic acid molecules of the invention.

The method for reducing the activity of the enzymes of the invention in the plant cells by means of a cosuppression effect is known to the skilled person and has been described, for example, in Jorgensen (Trends Biotechnol. 8 (1990), 340–344), Niebel et al. (Curr. Top. Microbiol. Immunol. 197 (1995), 91–103), Flavell et al. (Curr. Top. Microbiol. Immunol. 197 (1995), 4346), Palaqui and Vaucheret (Plant. Mol. Biol. 29 (1995), 149–159), Vaucheret et al. (Mol. Gen. Genet. 248 (1995), 311–317), de Borne et al. (Mol. Gen. Genet. 243 (1994), 613–621) and other sources.

The expression of ribozymes for reducing the activity of certain enzymes in cells is also known to the skilled person and has for example been described in EP-B1 0 321 201. The expression of ribozymes in plant cells has e.g. been described by Feyter et al. (Mol. Gen. Genet. 250 (1996), 329–338).

In order to reduce the activity of a protein of the invention antisense-RNA is preferably expressed in plant cells.

In order to express an antisense-RNA, on the one hand a DNA molecule can be used which comprises the complete sequence encoding a protein of the invention, including possibly existing flanking sequences as well as DNA molecules, which only comprise parts of the coding sequence whereby these parts have to be long enough in order to prompt an antisense-effect within the cells. Basically, sequences with a minimum length of 15 bp, preferably with a length of 100–500 bp and for an efficient antisense-inhibition, in particular sequences with a length of more than 500 bp may be used. Generally DNA molecules are used which are shorter than 5000 bp, preferably sequences with a length of less than 2500 bp.

Use may also be made of DNA sequences which are highly homologous, but not completely identical to the sequences of the DNA molecules of the invention. The minimal homology should be more than about 65%. Preferably, use should be made of sequences with homologies between 95 and 100%.

Maize plants containing the transgenic maize plant cells of the invention are also the subject matter of the invention. The invention also relates to the propagation material of the plants of the invention, in particular to seeds.

The starch obtainable from the above-described transgenic maize plant cells, maize plants and propagation material is also a subject matter of the invention.

Due to the reduction of the activity of a protein of the invention, the transgenic maize plant cells and maize plants synthesize a starch which compared to starch synthesized in wildtype plants is modified, for example, in its physicochemical properties, in particular in the amylose/amylopectin ratio, the degree of branching, the average chain-length, the phosphate-content, the pastification behavior, the size of the starch granule and/or the shape of the starch granule. Compared with wildtype-starch, such starch may be modified in particular with respect to its viscosity and/or the gel formation properties of the glues of this starch.

The starches of the invention may be modified according to techniques known to the skilled person; in unmodified as well as in modified form they are suitable for the use in foodstuffs and for the use in non-foodstuffs.

Basically, the possibilities of uses of the starch can be subdivided into two major fields. One field comprises the hydrolysis products of starch, essentially glucose and glucans components obtained by enzymatic or chemical processes. They can be used as starting material for further chemical modifications and processes, such as fermentation. In this context, it might be of importance that the hydrolysis process can be carried out simply and inexpensively. Currently, it is carried out substantially enzymatically using amyloglucosidase. It is conceivable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The other field in which the starch is used because of its polymer structure as so-called native starch, can be subdivided into two further areas:

1. Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

A preferred area of application of native starch is the field of bakery-goods and pasta.

2. Use in Non-foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

2.1 Paper and Cardboard Industry

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive Industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textile and Textile Care Industry

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building Industry

The fourth area of application of starch is its use as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground Stabilization

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

2.6 Use of Starch in Plant Protectives and Fertilizers

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, Medicine and Cosmetics Industry

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

2.8 Starch as an Additive in Coal and Briquettes

The use of starch as an additive in coal and briquettes is also conceivable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

2.9 Processing of Ore and Coal Slurry

Furthermore, the starch may be used as a flocculant in the processing of ore and coal slurry.

2.10 Starch as an Additive in Casting

Another field of application is the use as an additive to process materials in casting. For various casting processes cores produced from sands mixed with binding agents are needed. Nowadays, the most commonly used binding agent is bentonite mixed with modified starches, mostly swelling starches. The purpose of adding starch is increased flow resistance as well as improved binding strength. Moreover, swelling starches may fulfill more prerequisites for the production process, such as dispersability in cold water, rehydratisability, good mixability in sand and high capability of binding water.

2.11 Use of Starch in Rubber Industry

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

2.12 Production of Leather Substitutes

Another field of application for the modified starch is the production of leather substitutes.

2.13 Starch in Synthetic Polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known to the person skilled in the art. These are particularly modifications by means of heat treatment acid treatment oxidation and esterification leading to the formation of phosphate, nitrate, sulfate, xanthate, acetate and citrate starches. Other organic acids may also be used for the esterification:

formation of starch ethers starch alkyl ether, O-allyl ether, hydroxylalkyl ether, O-carboxylmethyl ether, N-containing starch ethers, P-containing starch ethers and S-containing starch ethers.

formation of branched starches formation of starch graft polymers.

In order to express the nucleic acid molecules of the invention in sense- or antisense-orientation in plant cells, these are normally linked to regulatory DNA elements which ensure the transcription in plant cells. Such regulatory DNA elements are particularly promoters. Basically any promoter which is active in plant cells may be used for the expression.

The promoter may be selected in such a way that the expression takes place constitutively or only in a certain tissue, at a certain point of time of the plant development or at a point of time determined by external circumstances. With respect to the plant the promoter may be homologous or heterologous. Suitable promoters for a constitutive expression are, e.g. the 35S RNA promoter of the Cauliflower Mosaic Virus and the ubiquitin promoter from maize. For a tuber-specific expression in potatoes the patatin gene promoter B33 (Rocha-Sosa et al., EMBO J. 8 (1989), 23–29) can be used. A promoter which ensures expression only in photosynthetically active tissues is, e.g. the ST-LS1 promoter (Stockhaus et al., Proc. Natl. Acad. Sci. USA 84 (1987), 7943–7947; Stockhaus et al., EMBO J. 8 (1989), 2445–2451). For an endosperm-specific expression the HMG promoter from wheat, the USP promoter, the phaseolin promoter or promoters from zein genes from maize are suitable.

Furthermore, a termination sequence may exist which serves to correctly end the transcription and to add a poly-A-tail to the transcript which is believed to stabilize the transcripts. Such elements are described in the literature (cf. Gielen et al., EMBO J. 8 (1989), 23–29) and can be exchanged as desired.

The present invention provides nucleic acid molecules encoding a novel type of soluble starch synthase identified in maize. This allows for the identification of the function of this starch synthase in the starch biosynthesis as well as for the production of genetically modified plants in which the activity of this enzyme is modified. This enables the synthesis of starch with a modified structure and therefore with modified physico-chemical properties in the plants manipulated in such a way.

Principally, the nucleic acid molecules of the invention may also be used in order to produce plants in which the activity of the starch synthase of the invention is elevated or reduced and in which at the same time the activities of other enzymes involved in the starch biosynthesis are modified. Thereby, all kinds of combinations and permutations are conceivable. By modifying the activities of one or more isotypes of starch synthases in plants, a synthesis of a starch modified in its structure is brought about. By increasing the activity of one or more isotypes of the starch synthase in cells of starch-storing tissues of transformed plants, for example in the endosperm of maize or wheat or in the tuber in the case of potato, also an increase in the yield may be achieved. For example, nucleic acid molecules encoding a protein of the invention, or corresponding antisense-constructs may be introduced into the plant cells, in which the synthesis of endogenous GBSS I-, SSS- or GBSS II-proteins is already inhibited due to an antisense-effect or a mutation, or in which the synthesis of the branching enzyme is inhibited (as described e.g. in WO92/14827 or in the ae-mutant (Shannon and Garwood, 1984, in Whistler, BeMiller and Paschall, Starch: Chemistry and Technology, Academic Press, London, $2^{nd}$ Edition: 25–86)).

If the inhibition of the synthesis of several starch synthases in transformed plants is to be achieved, DNA molecules can be used for transformation, which at the same time contain several regions in antisense-orientation controlled by a suitable promoter and encoding the corresponding starch synthases. Each sequence may be controlled by its own promoter or else the sequences may be transcribed as a fusion from a common promoter. The last alternative will generally be preferred as in this case the synthesis of the respective proteins should be inhibited to approximately the same extent. Furthermore, it is possible to generate molecules which comprise further DNA sequences coding for other proteins involved in starch synthesis or modification apart from DNA sequences coding for starch synthases. These sequences are linked to a suitable promoter. Again, the sequences may be linked directly to each other and may be transcribed from a common promoter. For the length of the single coding regions used in such a construct the same applies which has already been said above in connection with the production of antisense-constructs. There is no upper limit for the amount of the antisense fragments transcribed by a promoter in such a DNA molecule. The produced transcript, however, should usually not be longer than 10 kb or, preferably, 5 kb.

Coding regions which are localized in such DNA molecules in combination with other coding regions in antisense orientation behind a suitable promoter may be derived from DNA sequences coding for the following proteins: granule-bound (GBSS I and II) and soluble starch synthases (SSS I and II), branching enzymes, debranching enzymes, disproportioning enzymes and starch phosphorylases. This enumeration only serves as an example. The use of other DNA sequences is also conceivable within the framework of such a combination.

By means of such constructs it is possible to simultaneously inhibit the synthesis of a number of enzymes in plant cells transformed therewith.

Furthermore, the constructs may be inserted into classical mutants which are deficient for at least one gene of the starch biosynthesis (Shannon and Garwood, 1984, in Whistler, BeMiller and Paschall, Starch: Chemistry and Technology, Academic Press, London, $2^{nd}$ edition: 25–86). These deficiencies may relate to the following proteins: granule-bound (GBSS I and II) and soluble starch synthases (SSS I and II), branching enzymes (BE I and II), debranching enzymes (R enzymes), disproportioning enzymes and starch phosphorylases. This enumeration only serves as an example.

By proceeding in such a way it is furthermore possible to simultaneously inhibit the synthesis of a number of enzymes in plant cells transformed therewith.

In order to prepare the introduction of foreign genes into higher plants a multitude of cloning vectors is available comprising a replication signal for $E.$ $coli$ and a marker gene for the selection of transformed bacterial cells. Examples for such vectors are pBR322, pUC series, M13mp series, pACYC184 etc. The desired sequence may be integrated into the vector at a suitable restriction site. The obtained plasmid is used for the transformation of $E.$ $coli$ cells. Transformed $E.$ $coli$ cells are cultivated in a suitable medium and subsequently harvested and lysed. The plasmid is recovered. As an analyzing method for the characterization of the obtained plasmid DNA use is generally made of restriction analyses, gel electrophoreses and other biochemico-molecularbiological methods. After each manipulation the plasmid DNA may be cleaved and the obtained DNA fragments may be linked to other DNA sequences. Each plasmid DNA sequence may be cloned into the same or in other plasmids.

In order to introduce DNA into plant host cells a wide range of techniques are at disposal. These techniques comprise the transformation of plant cells with T-DNA by using Agrobacterium tumefaciens or Agrobacterium rhizogenes as transformation medium, the fusion of protoplasts, the injection and the electroporation of DNA, the introduction of DNA by means of the biolistic method as well as further possibilities.

In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should be present.

Depending on the method of introducing desired genes into the plant cell, further DNA sequences may be necessary. If the Ti- or Ri-plasmid is used e.g. for the transformation of the plant cell, in general at least the right border, more frequently, however, the right and left border of the Ti- and Ri-plasmid T-DNA should be connected to the foreign gene to be introduced as a flanking region.

If Agrobacteria are used for the transformation, the DNA which is to be introduced should advantageously be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to Agrobacterium tumefaciens (conjugation). Binary vectors may replicate in E. coli as well as in Agrobacteria. They contain a selectable marker gene as well as a linker or polylinker which is framed by the right and the left T-DNA border region. They may be transformed directly into the Agrobacteria (Holsters et al. Mol. Gen. Genet. 163 (1978), 181–187). The Agrobacterium acting as host cell should contain a plasmid carrying a vir-region. The vir-region is necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

For transferring the DNA into the plant cells, plant explants may suitably be co-cultivated with Agrobacterium tumefaciens or Agrobacterium rhizogenes. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the integrated DNA is present or not. Other possibilities in order to integrate foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H. J. Rehm, G. Reed, A. Puhler, P. Stadler, editors), Vol. 2, 627–659, VCH Weinheim-New York-Basel-Cambridge).

Whereas the transformation of dicotyledonous plants by Ti-plasmid-vector systems by means of Agrobacterium tumefaciens is a well-established method, more recent studies indicate that the transformation with vectors based on Agrobacterium can also be used in the case of monocotyledonous plants (Chan et al., Plant Mol. Biol. 22 (1993), 491–506; Hiei et al., Plant J. 6 (1994), 271–282).

Alternative systems for the transformation of monocotyledonous plants are the transformation by means of the biolistic approach, protoplast transformation, electroporation of partially permeabilized cells, the introduction of DNA by means of glass fibers.

There are various references in the relevant literature dealing specifically with the transformation of maize (cf. e.g. WO95/06128, EP 0 513 849; EP 0 465 875). In EP 292 435 a method is described by means of which fertile plants may be obtained starting from mucousless, friable granulous maize callus. In this context it was furthermore observed by Shillito et al. (Bio/Technology 7 (1989), 581) that for regenerating fertile plants it is necessary to start from callus-suspension cultures from which a culture of dividing protoplasts can be produced which is capable to regenerate to plants. After an in vitro cultivation period of 7 to 8 months Shillito et al. obtain plants with viable descendants which, however, exhibited abnormalities in morphology and reproductivity.

Prioli and Söndahl (Bio/Technology 7 (1989), 589) have described how to regenerate and to obtain fertile plants from maize protoplasts of the Cateto maize inbreed Cat 100-1. The authors assume that the regeneration of protoplast to fertile plants depends on a number of various factors such as the genotype, the physiological state of the donor-cell and the cultivation conditions.

Once the introduced DNA has been integrated in the genome of the plant cell, it usually continues to be stable there and also remains within the descendants of the originally transformed cell. It usually contains a selectable marker which confers resistance against biozides or against an antibiotic such as kanamycin, G 418, bleomycin, hygromycin or phosphinotricine etc. to the transformed plant cells. The individually selected marker should therefore allow for a selection of transformed cells against cells lacking the introduced DNA.

The transformed cells grow in the usual way within the plant (see also McCormick et al., Plant Cell Reports 5 (1986), 81–84). The resulting plants can be cultivated in the usual way and cross-bred with plants having the same transformed genetic heritage or another genetic heritage. The resulting hybrid individuals have the corresponding phenotypic properties.

Two or more generations should be grown in order to ensure whether the phenotypic feature is kept stably and whether it is transferred. Furthermore, seeds should be harvested in order to ensure that the corresponding phenotype or other properties will remain.

Figure 1:
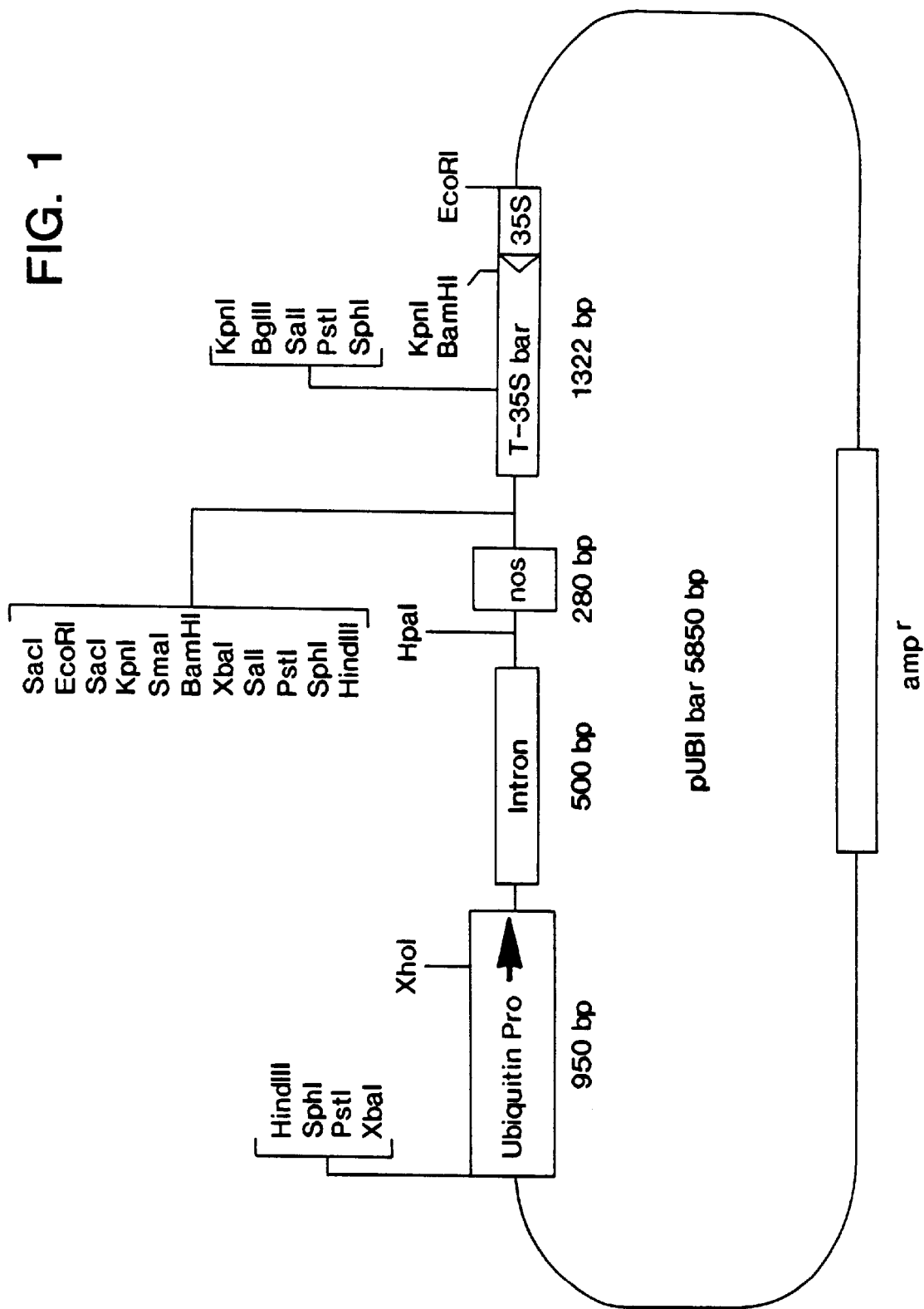
FIG. 1 schematically shows the vector pUBIbar

Ubiquitin-Pro = ubiquitin promoter
intron = intron from maize
nos = termination signal of the nopaline synthase gene from A. tumefaciens
35S = 35S promoter of CaMV
T35S = 35S terminator of CaMV FIG. 2 schematically shows the vector pUBI-bar-aMasy Ubiquitin-Pro = ubiquitin promoter
intron = intron from maize
nos = termination signal of the nopaline synthase gene from A. tumefaciens
35S = 35S promoter of CaMV
T35S = 35S terminator of CaMV This vector contains the cDNA encoding a starch synthase from maize as described in Example 1 in antisense-orientation to the ubiquitin promoter.

DETAILED DESCRIPTION OF THE INVENTION

The examples illustrate the invention.
Media and solutions used in the examples:

| | | |
|---|---|---|
| 20 × SSC | 175.3 | g NaCl |
| | 88.2 | g sodium citrate |
| | ad 1000 | ml with ddH$_2$O |
| | pH 7.0 with 10 | N NaOH |
| YT | 8 | g Bacto-Yeast extract |
| | 5 | g Bacto-Tryptone |
| | 5 | g NaCl |
| | ad 1000 | ml with ddH$_2$O |

Protoplast isolation medium (100 ml)

| | |
|---|---|
| Cellulase Onozuka R S (Meiji Seika, Japan) | 800 mg |
| Pectolyase Y23 | 40 mg |
| KNO$_3$ | 200 mg |
| KH$_2$PO$_4$ | 136 mg |
| K$_2$HPO$_4$ | 47 mg |
| CaCl$_2$ 2H$_2$O | 147 mg |
| MgSO$_4$ 7H$_2$O | 250 mg |
| Bovine serum albumine (BSA) | 20 mg |
| Glucose | 4000 mg |
| Fructose | 4000 mg |
| Sucrose | 1000 mg |
| pH | 5.8 |
| Osmolarity | 660 mosm. |

Protoplast washing solution 1: like protoplast isolating solution, but without cellulase, pectolyase and BSA Transformation buffers:

| | | |
|---|---|---|
| a) | Glucose | 0.5 M |
| | MES | 0.1% |
| | MgCl$_2$ 6H$_2$O | 25 mM |
| | pH | 5.8 |
| | adjust to 600 mosm. | |
| b) | PEG 6000-solution | |
| | Glucose | 0.5 M |
| | MgCl$_2$ 6H$_2$O | 100 mM |
| | Hepes | 20 mM |
| | pH | 6.5 |

PEG 6000 is added to the buffer described in b) immediately prior to the use of the solution (40% w/v PEG). The solution is filtered with a 0.45 μm sterile filter.

W5 solution

| | |
|---|---|
| CaCl$_2$ | 125 mM |
| NaCl | 150 mM |
| KCl | 5 mM |
| Glucose | 50 mM |

Protoplast culture medium (indicated in mg/l)

| | |
|---|---|
| KNO$_3$ | 3000 |
| (NH$_4$)$_2$SO$_4$ | 500 |
| MgSO$_4$ 7H$_2$O | 350 |
| KH$_2$PO$_4$ | 400 |
| CaCl$_2$ 2H$_2$O | 300 |

Fe-EDTA and trace elements as in the Murashige-Skoog medium (Physiol. Plant, 15 (1962), 473).

| | |
|---|---|
| m-inosite | 100 |
| Thiamine HCl | 1.0 |
| Nicotine acid amide | 0.5 |
| Pyridoxine HCl | 0.5 |
| Glycine | 2.0 |
| Glucuronic acid | 750 |
| Galacturonic acid | 750 |
| Galactose | 500 |
| Maltose | 500 |
| Glucose | 36,000 |
| Fructose | 36,000 |
| Sucrose | 30,000 |
| Asparagine | 500 |
| Glutamine | 100 |
| Proline | 300 |
| Caseinhydrolysate | 500 |
| 2,4 dichlorophenoxy acetic acid (2,4-D) | 0.5 |
| pH | 5.8 |
| Osmolarity | 600 mosm. |

In the examples the following methods were used:

1. Cloning Methods

For cloning in *E. coli* the vector pBluescript II SK (Stratagene) was used.

2. Bacterial Strains

For the Bluescript vector and for the pUSP constructs use was made of the *E. coli* strain DH5α (Bethesda Research Laboratories, Gaithersburgh, USA).

The *E. coli* strain XL1-Blue was used for in vivo excision.

3. Transformation of Maize (a) Production of Protoplasts of the Cell Line DSM 6009

Protoplast isolation

2–4 days, preferably 3 days after the last change of medium in a protoplast suspension culture the liquid medium is pumped off and the remaining cells are washed in 50 ml protoplast washing solution 1 and sucked dry once more. 10 ml protoplast isolation medium are added to 2 g of harvested cell mass. The resuspended cells and cell aggregates are incubated at 27±2° C. for 4 to 6 hours in the darkness, while shaking it slightly (at 30 to 40 rpm).

Protoplast Purification

As soon as the release of at least 1 million protoplasts/ml has taken place (microscopic inspection), the suspension is sifted through a stainless steel or nylon sieve with a mesh size of 200 or 45 μm. The combination of a 100 μm and a 60 μm sieve allows for separating the cell aggregates just as well. The protoplast-containing filtrate is examined microscopically. It usually contains 98–99% protoplasts. The rest are undigested single cells. Protoplast preparations with such a degree of purity are used for transformation experiments without additional gradient centrifugation. The protoplasts are sedimented by means of centrifugation (100 UpM in the swing-out rotor (100×g, 3 minutes)). The supernatant is abandoned and the protoplasts are resuspended in washing solution 1. The centrifugation is repeated and the protoplasts are subsequently resuspended in the transformation buffer.

(b) Protoplast Transformation

The protoplasts resuspended in the transformation buffer are filled in 10 ml portions into 50 ml polyallomer tubes at a titer of 0.5–1×10⁶ protoplasts/ml. The DNA used for transformation is dissolved in Tris-EDTA (TE) buffer solution. 20 µg plasmid DNA is added to each ml protoplast suspension. A plasmid which provides for resistance to phosphinotricine is used as vector (cf. e.g. EP 0 513 849). After the addition of DNA the protoplast suspension is carefully shaken in order to homogenously distribute the DNA in the solution. Immediately afterwards 5 ml PEG solution is added in drops.

By carefully shaking the tubes the PEG solution is distributed homogeneously. Afterwards further 5 ml of PEG solution are added and the homogenous mixing is repeated. The protoplasts remain in the PEG solution for 20 minutes at ±2° C. Afterwards the protoplasts are sedimented by centrifuging for 3 minutes (10 g; 1000 Upm). The supernatant is abandoned. The protoplasts are washed in 20 ml W5 solution by careful shaking and are again subjected to centrifugation. Then they are resuspended in 20 ml protoplast culture medium, centrifuged anew and again resuspended in culture medium. The titer is adjusted to 6–8×10⁵ protoplasts and the protoplasts are cultivated in 3 ml portions in Petri dishes (Ø 60 mm, height 15 mm). The Petri dishes are sealed with parafilm and stored in darkness at 25±2° C.

(c) Protoplast Culture

During the first 2–3 weeks after the protoplast isolation and transformation the protoplasts are cultivated without adding fresh medium. As soon as the cells regenerated from the protoplasts have developed into cell aggregates with more than 20 to 50 cells, 1 ml of fresh protoplast culture medium, containing sucrose as an osmotic (90 g/l), is added.

(d) Selection of Transformed Maize Cells and Plant Regeneration

3–10 days after adding fresh medium the cell aggregates developed from the protoplasts may be plated on Agar media with 100 mg/l L-phosphinothricine. N6-medium with the vitamins of the protoplast culture medium, 90 g/l sucrose and 1.0 mg/l 2,4D is as suitable as an analogous medium such as a medium with the macro- and micro-nutritive salts of the MS medium (Murashige and Skoog (1962), see above).

The calli developed from stably transformed protoplasts may grow further on the selective medium. After 3 to 5 weeks, preferably 4 weeks the transgenic calli may be transferred to fresh selection medium which also contains 100 mg/l L-phosphinothricine which, however, does no longer contain auxine. Within 3 to 5 weeks approximately 50% of the transgenic maize calli which had integrated the L-phosphinothricine-acetyl-transferase gene into their genome, start to differentiate into plants on this medium in the presence of L-phosphinothricine.

(e) Growing of Transgenic Regenerative Plants

The embryogenical transformed maize tissue is cultivated on hormone-free N6-medium (Chu C. C. et al., Sci. Sin. 16 (1975), 659) in the presence of 5×10⁻⁴ M L-phosphinothricine. On this medium maize embryos, which express the phosphinothricine-acetyl-transferase gene (PAT gene) in a sufficiently strong manner, develop into plants. Non-transformed embryos or such with only a very weak PAT activity die down. As soon as the leaves of the in-vitro plants have reached a length of 4 to 6 mm, they may be transferred into soil. After washing off the Agar residues at the roots the plants are planted into a mixture of clay, sand, vermiculite and potting soil with the ratio 3:1:1:1 and adapted to the soil culture at 90–100% of relative atmospheric humidity during the first 3 days after planting. The growing is carried out in a climate chamber with a 14 hour light period of approximately 25000 lux at the height of the plant at a day/night temperature of 23±1/17±1° C. The adapted plants are cultivated at an 65±5% atmospheric humidity.

4. Radioactive Marking of DNA Fragments

The radioactive marking of DNA fragments was carried out by means of a DNA-Random Primer Labeling Kits by Boehringer (Germany) according to the manufacturer's instructions.

EXAMPLE 1

Identification, Isolation and Characterization of a cDNA Encoding a Novel Isotype of a Starch Synthase from Maize In order to isolate a novel soluble starch synthase from maize, polyclonal antibodies against peptide 1 were produced.

Peptide 1: NH₂-GTGGLRDTVENC-COOH (Seq. ID No. 3)

This peptide was coupled to the KLH carrier (keyhole limpet homocyanin") and subsequently used for producing polyclonal antibodies in rabbits (Eurogentec, Seraing, Belgium).

The resulting antibody was designated anti-SS1.

Subsequently, the anti-SS1 antibody was used in order to screen a cDNA library from maize for sequences encoding soluble starch synthases from maize. For this purpose, a cDNA library from endosperm polyA⁺ RNA, constructed in the λ-ZAP vector, was used. In order to analyze the phage plaques, they were transferred onto nitrocellulose filters which had before been incubated in 10 mM IPTG solution for 30–60 min. and subsequently dried on filtering paper. The transfer took place at 37° C. for 3 hours. The filters were subsequently incubated in blocking reagent for 30 min. at room temperature and.washed twice in TBST buffer for 5 to 10 min. The filters were shaken with the polyclonal antibody anti-SS1 in a suitable dilution for 1 h at room temperature or for 16 h at 4° C. The identification of plaques which expressed a protein which was recognized by the anti-SS1 antibody was carried out by means of the "blotting detection kit for rabbit antibodies RPN 23" (Amersham UK) according to the manufacturer's instructions.

Phage clones of the cDNA library expressing a protein which was recognized by the anti-SS1 antibody were purified according to standard methods. By means of the in vivo excision method (Stratagene), E. coli clones were obtained from positive phage clones, containing a double-stranded pBlueskript II SK plasmid with the respective cDNA insert between the EcoRI and the Xho I site of the polylinker. After checking the size and the restriction pattern of the insert, a suitable clone was subjected to a sequence analysis.

EXAMPLE 2

Sequence Analysis of the cDNA Insert of the Plasmid pSSS1

The plasmid pSSS1 was isolated from the E. coli clone which was obtained as described in Example 1 and its cDNA insert was determined in a standard routine by means of the didesoxynucleotide-method (Sanger et al., Proc. Natl. Acad. Sci. USA 74 (1977), 5463–5467). The insert has a length of 2383 bp and constitutes a partial cDNA. The nucleotide sequence is indicated under Seq ID No. 1. The corresponding amino acid sequence is indicated under Seq ID No. 2.

A sequence analysis and a comparison with known sequences showed that the sequence shown under Seq ID No. 1 is novel and encodes a type I soluble starch synthase from maize. The partial coding region exhibits homology to starch synthases from various other organisms, in particular to a starch synthase from rice. Within the framework of this application, the protein encoded by this cDNA insert or by hybridizing sequences is named SSS1Zm. By means of this partial cDNA sequence it is possible for the person skilled in the field of molecular biology to isolate full-length clones comprising the complete coding region and to determine their sequences without any further ado. In order to do so, e.g. a leaf-specific cDNA expression library from Zea mays, line B73 (Stratagene GmbH, Heidelberg) is screened for full-length clones according to standard methods by means of hybridization with a 5'-fragment of the cDNA insert of the plasmid pSSS1 (200 bp). The clones obtained in such a way are subsequently sequenced. On the other hand the missing terminal 5'-sequences may be obtained by using the 5'-Race-method (e.g. of Stratagene or other manufacturers).

EXAMPLE 3

Construction of the Plant Transformation Vector pUBI-bar-aMASY and Production of Transgenic Maize Plants In order to produce a plant transformation vector encoding an antisense-RNA for a nucleic acid molecule of the invention, the vector pUBIbar (see FIG. 1) was linearized with the restriction enzyme HpaI and dephosphorylized with alkaline phosphatase. The cDNA isolated according to Example 1 (approximately 2.4 kb) was cloned into the linearized vector; the cDNA had been obtained from the pBluescriptSK plasmid as EcoRV/SmaI fragment. By means of restriction analysis a plasmid was identified which contained the cDNA encoding the starch synthase from maize in antisense-orientation to the promoter. This plasmid was designated pUBI-bar-aMasy. This vector contains an ubiquitin promoter and an intron from maize (Christensen et al., Plant Mol. Biol. 18 (1992), 675–689), the transcription termination signal of the nopaline synthase gene from A. tumefaciens (Depicker et al., J. Mol. Appl. Genet. 1 (1982), 561–573), the bar marker gene (Thompson et al., EMBO J. 6 (1987), 2519–2523) which comprises the coding region of the bialaphos resistance gene from Streptomyces hygroscopicus, as well as the 35S promoter and terminator of CaMV (Franck et al., Cell 21 (1980), 285–294) in connection with the bar gene. Furthermore, the plasmid contains the cDNA encoding the starch synthase from maize in antisense-orientation to the ubiquitin promoter between the intron and the nos-terminator.

The plasmid is represented in FIG. 2.

The vector pUBI-bar-aMasy was introduced into maize protoplasts by means of the above-described method. Thereby, $4.8 \times 10^7$ protoplasts and 100 μg plasmid DNA were used.

408 phosphinothricine-resistant clones were obtained. Among those, 40 were analyzed with respect to the expression of the introduced DNA. The result was that 12 of the obtained clones expressed the introduced DNA. Six of these clones were regenerated to whole plants and transferred into the greenhouse.

---

What is claimed is:

1. An isolated nucleic acid molecule comprising a nucleic acid sequence encoding a protein with the biological activity of a type I soluble starch synthase or comprising the complementary strand of said nucleic acid sequence, wherein the nucleic acid sequence is selected from the group consisting of:

(a) a nucleic acid sequence encoding a protein comprising the amino acid sequence of SEQ ID NO: 2;

(b) a nucleic acid sequence that is the coding region of SEQ ID NO: 1;

(c) a nucleic acid sequence that has more than 90% sequence identity to the entire coding region of SEQ ID NO: 1;

(d) a fragment of the nucleic acid sequence of (a), (b) or (c), wherein the fragment encodes a protein which has the biological activity of a type I soluble starch synthase; and (e) a nucleic acid sequence that deviates from the sequence of any one of the nucleic acid sequences of (a), (b), (c) or (d) due to the degeneracy of the genetic code.

2. The isolated nucleic acid molecule according to claim 1, wherein the molecule is a DNA molecule.

3. The nucleic acid molecule according to claim 2, wherein the DNA molecule is a cDNA molecule.

4. The isolated nucleic acid molecule according to claim 1, wherein the molecule is an RNA molecule.

5. The isolated nucleic acid molecule according to claim 1, wherein the nucleic acid sequence has more than 90% sequence identity to the entire coding region of SEQ ID NO: 1.

6. An isolated nucleic acid molecule comprising a nucleic acid sequence encoding a protein with the biological activity of a type I soluble starch synthase, wherein the nucleic acid sequence is between 95% and 100% identical to the entire coding region of SEQ ID NO: 1.

7. The isolated nucleic acid molecule according to claim 1, wherein the nucleic acid sequence is the coding region of SEQ ID NO: 1.

8. The isolated nucleic acid molecule according to claim 1, wherein the nucleic acid sequence encodes a protein comprising the amino acid sequence of SEQ ID NO:2.

9. An isolated nucleic acid molecule comprising a nucleic acid sequence that deviates from the nucleic acid sequence of the nucleic acid molecule according to claim 6 due to the degeneracy of the genetic code.

10. An isolated nucleic acid molecule comprising a fragment of the nucleic acid sequence of the nucleic acid molecule according to claim 6, wherein the fragment encodes a protein which has the biological activity of a type I soluble starch synthase.

11. An isolated nucleic acid molecule comprising a fragment of the nucleic acid sequence of the nucleic acid molecule according to claim 7, wherein the fragment encodes a protein which has the biological activity of a type I soluble starch synthase.

12. An isolated nucleic acid molecule comprising a fragment of the nucleic acid sequence of the nucleic acid molecule according to claim 8, wherein the fragment encodes a protein which has the biological activity of a type I soluble starch synthase.

13. An isolated nucleic acid molecule comprising the nucleic acid sequence of SEQ ID NO: 1.

14. A vector comprising the nucleic acid molecule according to any one of claims 1, 5–7, 8, or 9–13.

15. The vector according to claim 14, wherein the nucleic acid molecule is linked in sense-orientation to regulatory elements which ensure the transcription and the synthesis of a translatable RNA in prokaryotic or eukaryotic cells.

16. A host cell that is genetically modified with the nucleic acid molecule according to any one of claims 1, 5–7, 8, or 9–13, or with a vector comprising said nucleic acid molecule.

17. A method for the production of a protein encoded by the nucleic acid molecule according to any one of claims 1, 5–7, 8, or 9–13 or a biologically active fragment thereof, comprising the step of cultivating a host cell that is genetically modified with said nucleic acid molecule or a vector comprising said nucleic acid molecule under conditions that allow for the synthesis of the protein or the fragment, and collecting the protein from the cultivated cells, the culture medium, or both the cultivated cells and the culture medium.

18. A transgenic plant cell genetically modified with the nucleic acid molecule according to any one of claims 1, 5–7, 8, or 9–13 or comprising a vector comprising said nucleic acid molecule wherein the nucleic acid molecule is subject to the control of regulatory elements allowing for the transcription of a translatable mRNA in plant cells.

19. A plant comprising the plant cell according to claim 18.

20. The plant according to claim 19, wherein the plant is a starch-storing or starch-synthesizing plant.

21. The plant according to claim 20, wherein the plant is a starch-storing plant.

22. The plant according to claim 21, wherein the plant is a maize plant.

23. A propagation material of the plant according to claim 19.

24. A transgenic plant cell that has a recombinant DNA molecule integrated into the genome of the plant cell, wherein the recombinant DNA molecule comprises:
   (a) a promoter active in plant cells; and
   (b) the nucleic acid molecule according to any one of claims 1, 5–7, 8, or 9–13 wherein the expression of said nucleic acid sequence leads to a cosuppression effect for a type I soluble starch synthase in the plant cell.

25. A maize plant comprising a plant cell according to claim 18.

26. A propagation material of the maize plant according to claim 18.

27. The plant of claim 20, wherein the plant is selected from the group consisting of rye, barley, oats, wheat, rice, maize, pea, cassava and potato.

* * * * *

UNITED STATES PATENT AND TRADEMARK OFFICE
CERTIFICATE OF CORRECTION

PATENT NO. : 6,307,124 B1
DATED : October 23, 2001
INVENTOR(S) : Jen Kossmann et al.

It is certified that error appears in the above-identified patent and that said Letters Patent is hereby corrected as shown below:

<u>Column 2,</u>
Lines 8, 17, 36, 37 and 38, change "synthesis" to -- synthases --.

<u>Column 3,</u>
Line 13, change "448453" to -- 448-453 --.

<u>Column 7,</u>
Line 38, change "NatI." to -- Natl. --.
Line 39, change "et a.," to -- et al., --.

<u>Column 8,</u>
Line 27, change "4346" to -- 43-46 --.

<u>Column 11,</u>
Line 7, change "andlor" to -- and/or --.

<u>Column 12,</u>
Line 48, change "heat" to -- - heat --.
Line 49, change "acid" to -- - acid --.
Line 50, change "oxidation" to -- - oxidation --.
Line 51, change "esterification" to -- - esterification --.
Line 56, change "formation of starch ethers starch alkyl ether, O-allyl ether," to
-- - formation of starch ethers
starch alkyl ether, O-allyl ether, --.
Lines 60 and 61, change "formation" to -- - formation --.

<u>Column 19,</u>
Line 18, change "10 g" to -- 100 g --.

<u>Column 20,</u>
Line 40, change "and.washed" to -- and washed --.

UNITED STATES PATENT AND TRADEMARK OFFICE
CERTIFICATE OF CORRECTION

PATENT NO.    : 6,307,124 B1
DATED         : October 23, 2001
INVENTOR(S)   : Jen Kossmann et al.

It is certified that error appears in the above-identified patent and that said Letters Patent is hereby corrected as shown below:

<u>Column 34,</u>
Line 2, change "claim 18" to -- claim 24 --.
Line 4, change "claim 18" to -- claim 25 --.

Signed and Sealed this

Twenty-fifth Day of June, 2002

Attest:

Attesting Officer

JAMES E. ROGAN
*Director of the United States Patent and Trademark Office*